United States Patent [19]

Oosawa et al.

[11] Patent Number: 4,582,808
[45] Date of Patent: Apr. 15, 1986

[54] SILVER STAINING METHOD

[75] Inventors: Kazuaki Oosawa; Nobuyoshi Ebata; Miyoshi Hirata, all of Tokyo, Japan

[73] Assignee: Daiichi Pure Chemicals Co., Ltd., Tokyo, Japan

[21] Appl. No.: 611,984

[22] Filed: May 18, 1984

[30] Foreign Application Priority Data

May 26, 1983 [JP] Japan .................................. 58-91487

[51] Int. Cl.$^4$ ...................... G01N 21/78; G01N 33/68
[52] U.S. Cl. ..................................... 436/86; 436/169; 436/177
[58] Field of Search .................... 436/86, 87, 169, 177

[56] References Cited

U.S. PATENT DOCUMENTS

| | | | |
|---|---|---|---|
| 3,997,656 | 12/1976 | Wertlake et al. | 8/94.33 |
| 4,416,998 | 11/1983 | Adams et al. | 436/86 |
| 4,468,466 | 8/1984 | Morrissey | 436/86 |

OTHER PUBLICATIONS

Ohsawa et al., Analytical Biochemistry, 135, 409–415 (1983).

Palumbo et al., Analytical Biochemistry, 134, 254–258 (1983).

Wayne Wray et al, "Silver Staining of Proteins in Polyacrylamide Gels", (Nov. 15, 1981), pp. 197–203 (Analytical Biochemistry).

Sammons et al, "Ultrasensitive Silver Based Color Staining of Polypeptides in Polyacrylamide Gels", (Feb. 1981), pp. 135–141, (Electrophoresis, vol. 2, no. 1).

Primary Examiner—Arnold Turk
Attorney, Agent, or Firm—Oblon, Fisher, Spivak, McClelland & Maier

[57] ABSTRACT

A silver staining method comprising the steps of (1) pretreating a carrier bearing thereon a substance to be detected with an alcoholic solution containing polyethylene glycol or polyoxyethylene alkylphenol, and (2) treating the pretreated carrier with a solution comprising silver nitrate, a compound of R—$NH_2$, and a caustic alkali in ratios by molecular weight of 1:4.5–9.5:1.0–26.0.

The method according to the invention involves advantages of high sensitivity and good reproducibility of detection, simple operation, safe handling etc.

13 Claims, 1 Drawing Figure

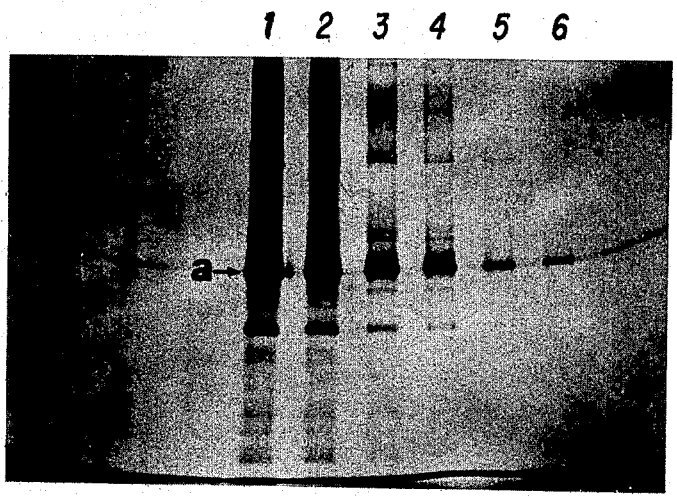

SILVER STAINING METHOD

BACKGROUND OF THE INVENTION (i) Field of the Invention

This invention relates to silver stain and more particularly, to a method for staining a carrier, which bears thereon substances being detected, with silver in which the carrier is pretreated with an neutral or approximately neutral alcoholic solution comprising polyethylene glycol or a polyoxyethylene alkylphenol and subsequently treated with a silver staining solution of a specific type.

(ii) Description of the Prior Art

At present, various detecting methods have been put into practice, of which attention has been recently paid to silver stain because of its relatively higher sensitivity than other methods. The silver staining method has been widely used since it allows electrophoretic analysis, of samples having a low concentration of a substance to be detected such as, for example, proteins, nucleic acids, sugars, and lipids. Examples of such samples are urine, cerebrospinal fluid, etc.

A number of methods for silver staining have been reported (SEIKAGAKU Vol. 52, page 411, 1980, Protein Nucleic Acid and Enzyme Vol. 27, page 1277, 1982, Electrophoresis Vol. 2, pages 141 and 135, 1981). However, all of the methods have the drawback that they require a long time to complete staining, and complicated operations are necessary because the procedure employed depends on the type of substance being detected. According to our experience, all the known staining methods also have the disadvantage of low reproducibility.

For instance, according to Poehling et al (Electrophoresis Vol. 2, 141, 1981), after electrophoresis, the carrier is fixed with a 50% methanol/10% acetic acid solution for 30 minutes, thereby suppressing coloration of the background of the carrier, and subsequently fixed with a 6% glutaraldehyde solution to increase the stain sensitivity. However, these reagents should be removed by washing with methanol and water several times. These pretreatments therefore require a long time.

SUMMARY OF THE INVENTION

In order to overcome the drawbacks of the prior art, we have made intensive studies and as a result, have found that when a carrier is treated with an alcoholic solution comprising polyethylene glycol or a polyoxyethylene alkylphenol, the carrier shrinks and becomes easy to wash, resulting in reduction of washing time. Furthermore, it was found that when a silver staining solution is prepared which has specific ratios of silver nitrate; a compound of the formula R—$NH_2$, wherein R—$NH_2$ represents ammonia or a primary amine; and a caustic alkali, it is possible to shorten the operation time and improve the reproducibility of staining.

According to the present invention, there is provided a silver staining method which comprises pretreating a carrier bearing thereon a substance to be detected with an alcoholic solution comprising alcohol and water and containing polyethylene glycol or polyoxyethylene alkylphenol; and treating the pretreated carrier with a solution comprising silver nitrate, a compound of the formula R—$NH_2$ (R—$NH_2$ has the same meaning as defined above) and a caustic alkali in ratios by molecular weight of 1:4.5–9.5:1.0–26.0.

BRIEF DESCRIPTION OF THE DRAWING

The FIGURE is a band image obtained according to Example 3 in which a is a band image of BSA, and 1, 2, 3, 4, 5 and 6 are, respectively, images obtained in electrophoresis of 5 ng, 1 ng, 500 pg, 100 pg, 50 pg and 10 pg of BSA.

DETAILED DESCRIPTION OF THE INVENTION AND PREFERRED EMBODIMENTS

In order to carry out the method of the present invention, a carrier which has been subjected to electrophoresis by a usual manner (hereinafter referred to simply as gels) is immersed in an alcoholic solution containing polyethylene glycol or a polyoxyethylene alkylphenol (hereinafter referred to as the washing and fixing solution) for about 10 to 60 minutes, preferably about 25 minutes, thereby causing the gels to shrink. By the shrinkage, the water and the reagent are released from the gels. The alcohols used in the washing and fixing solution include lower alcohols and preferably linear or branched alcohols having from 1 to 4 carbon atoms. Examples of such linear or branched alcohols include methanol, ethanol, propanol, isopropanol, butanol, isobutanol, and mixtures thereof. Of theses, isopropanol, or a mixture of methanol and ethanol is preferred. These alcohols are conveniently used as an aqueous solution having a concentration of from 30 to 70 (v/v)%, preferably about 50 (v/v)%.

Polyethylene glycol suitable for the purpose of the invention has an average molecular weight of from 600 to 3500, preferably 1500 to 2500. The polyoxyethylene alkylphenol is represented by the formula,

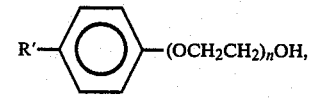

in which R' represents a linear or branched alkyl having from 6 to 10 carbon atoms, and n is an integer of 7 to 10 which indicates the center of the distribution. Preferably, in the above formula, R' is octyl and n is 9 which indicates the center of the distribution. The polyethylene glycol (PEG) or polyoxyethylene alkylphenol is generally used in a concentration of 0.05 to 5 (w/v)%, preferably about 2 (w/v)%, of the washing and fixing solution.

In the washing and fixing solution, if the concentration of alcohol is below 20 (v/v)%, the background of the gels is colored, making it difficult to confirm stained bands. On the other hand, when the concentration exceeds 90 (v/v)%, bands do not appear clearly. The concentration of polyethylene glycol or polyoxyethylene glycol below 0.01 (w/v)% is unfavorable because clear bands are not obtained. A concentration over 5 (w/v)% does not give any further effect.

The gels pretreated with the washing and fixing solution are subsequently immersed in and treated with a silver staining solution for 10 to 30 minutes, preferably about 15 minutes. The silver staining solution used for the above treatment is a mixture of silver nitrate, a compound of the formula R—$NH_2$ (R—$NH_2$ has the same meaning as defined before), and a caustic alkali in mixing ratios by molecular weight of 1:4.5–9.5:1.0–26.0. The treatment with the silver staining solution within the above mixing ratios permits staining with good reproducibility and a reduction of the operation time. It will be noted that when the mixing ratio of the R—NH$_2$ compound is below 4 and the mixing ratio of the caustic alkali is over 28 based on the molecular weight, considerable unfavorable precipitation of silver oxide takes place. On the other hand, when the mixing ratio by molecular weight of ammonia is over 10 and the mixing ratio of caustic alkali is below 0.5, it is difficult to stain the gels.

Compounds of the formula, R—NH$_2$, usable in the present invention include, for example, ammonia, ethanolamine, propanolamine, isopropanolamine, butanolamine, isbutanolamine, tris(hydroxymethyl)aminomethane, methylamine, ethylamine, propylamine, butylamine, isobutylamine, etc. Examples of the caustic alkali include sodium hydroxide, potassium hydroxide, etc.

The gels treated with the silver staining solution are then immersed in a developer solution for about 10 to 15 minutes. If necessary, after treatment with the developer, the gel may be further immersed in a solution of 0.5 to 2 (w/v)% chloroauric acid, by which a clearer image is obtained.

The method of the present invention is conveniently applied to polymerized gels having a network structure, such as polyacrylamide gel, agar-agar, agarose, etc.

The method of the invention and conventional methods are summarized in Table 1.

The method of the invention has the following features:

(1) Neither glutaraldehyde, which is unstable as a fixing agent, nor acids such as trichloroacetic acid, acetic acid, etc which involve danger in handling are needed;

(2) No operation of removing the fixing agent is necessary;

(3) The pretreatment is simple; and (4) High sensitivity and good reproducibility are obtained.

The present invention is described in detail by way of examples.

EXAMPLE 1

Gels were washed with washing and fixing solutions having different concentrations of alcohol and polyethylene glycol to allow determination of the presence or absence of bands and coloration on the background. The results are shown in Table 2.

Sample

A gel was obtained by subjecting a Hind III fragment of λ phage DNA to electrophoresis using polyacrylamide gel.

Reagents (1) Silver staining solution

TABLE 1

|  | Method of Invention | Poehling et al Method | Sammons et al Method |
|---|---|---|---|
| Pretreatment Step (Washing & Fixing Solution) | 50% isopropanol + 2% PEG 25 min. | 50% methanol + 10% acetic acid 30 min. 15% methanol 30 min 6% glutaraldehyde 30 min. 15% methanol Water 20 min. / 10 min. × 3 | 50% ethanol + 10% acetic acid 120 min. × 2 25% ethanol + 10% acetic acid 60 min. × 2 10% ethanol + 0.5% acetic acid 60 min. × 2 |
| Silver Staining Step (Silver Staining Solution) | Ammoniacal silver nitrate solution silver nitrate 1 ammonia 7 caustic soda 4.3 ratio by molecular wt. 15 min. | Ammoniacal silver nitrate solution silver nitrate 1 ammonia 9.2 caustic soda 0.34 ratio by molecular wt. 15 min. | Silver nitrate solution 120 min. |
| Washing Step | washing with water 5 min. | washing with water 6 min. | washing with water 10–20 seconds |
| Developing Step (developer) | 0.005% citric acid 0.02% formalin 15 min. | 0.005% citric acid 0.02% formalin 15 min. washing with water 10 min. × 3· | 3% caustic acid 0.009% sodium boron hydride 0.28% formalin 10 min. 0.75% sodium carbonate 60 min. × 2 0.75 sodium carbonate 360 min. |
| Total Time | 1 hour | 4.1 hours | 18 hours |

As will be seen from the above table, the method of the invention ensures formation of a clear image in about 60 minutes. Moreover, the same procedure may be applied to any substance contained in gels such as proteins, nucleic acids, sugars, lipids, etc.

Silver nitrate, ammonia and sodium hydroxide were dissolved in distilled water in ratios by molecular weight of 1:7:4.3 to make a total volume of 200 ml.

(2) Developer solution 0.05% citric acid, 37% formalin and distilled water were used to make 200 ml of a 0.02 v/v% formalin solution of 0.005 w/v% citric acid.

Operation

Each sample was immersed for 25 minutes in mixtures of isopropanol and polyethylene glycol 2000 having different concentrations indicated in Table 2, after which each sample was immersed in a silver staining solution for 15 minutes to cause the solution to penetrate into the gel. Thereafter, the sample was placed in a pan containing 200 ml of distilled water for washing. This procedure was repeated three times. Finally, the sample was immersed in a developer solution for 15 minutes with the result that a brown to black band image appeared.

TABLE 2

| Concentration of Isopropanol (v/v) % | Concentration of Polyethylene glycol (w/v) % | Evaluation* Presence or absence of bands | Background coloration |
|---|---|---|---|
| 0 |  | + | X |
| 10 |  | + | X |
| 30 | 2 | ++ | O |
| 50 |  | +++ | O |
| 70 |  | + | O |
| 90 |  | − | O |
|  | 0 | + | X |
|  | 0.01 | + | O |
|  | 0.05 | + | O |
|  | 0.1 | ++ | O |
| 50 | 1 | +++ | O |
|  | 2 | +++ | O |
|  | 4 | +++ | O |
|  | 6 | +++ | O |
|  | 10 | +++ | O |

*Evaluation Standard
Presence or Absence of Bands
+++ Band image is very clear.
++ Band image is clear.
+ Band image free of any practical problem obtained.
± Some problems are involved such as poor reproducibility, unclear band image, etc.
− No band image is obtained.
Background Coloration
O No coloration.
X Coloration.

EXAMPLE 2

A solution of 2 g/l of silver nitrate was provided, to which different amounts of sodium hydroxide and ammonia were added to vary ratios thereof by molecular weight. The presence or absence of bands was checked and the optimal mixing ratios were determined. The results are shown in Table 3. The sample, developing solution and operation procedure were the same as in Example 3 described hereinafter.

TABLE 3

| Ratio by M.W. of Ammonia | Ratio by M.W. of Caustic Alkali | | | | | | | | | |
|---|---|---|---|---|---|---|---|---|---|---|
|  | 0.53 | 1.06 | 2.13 | 4.25 | 8.5 | 12.75 | 17 | 21.25 | 26 | 29.75 |
| 3.15 | ± | ± | ± | ± | ± | ± | ± | ± | ± | ± |
| 4.0 | ± | ± | ± | ± | ± | ± | ± | ± | ± | ± |
| 4.73 | ± | + | + | ++ | ++ | + | + | + | + | ± |
| 6.3 | − | + | ++ | +++ | +++ | +++ | + | + | + | ± |
| 7.88 | − | + | + | +++ | +++ | ++ | + | + | + | ± |
| 9.5 | − | + | + | + | + | + | + | + | + | ± |
| 11.03 | − | ± | ± | ± | ± | ± | ± | ± | ± | ± |

The evaluation standard is the same as in Example 1.

EXAMPLE 3

Sample

A gel was obtained by subjecting bovine serum albumin to electrophoresis with sodium dodecylsulfatepolyacrylamide gel (hereinafter referred to simply as SDS-PAG).

Reagents (1) Washing and fixing solution
Isopropanol and polyethylene glycol 2000 (by Furuka A. G., Switzerland) were diluted with distilled water to make a total volume of 200 ml with concentrations of 50% (v/v) and 1% (w/v), respectively.

(2) Silver staining solution
Silver nitrate, ammonia and sodium hydroxide were dissolved in distilled water to have mixing ratios by molecular weight of 1:4.8:1. The total volume was brought up to 200 ml.

(3) Developer
0.05% citric acid, 37% formalin and distilled water was used to make a total 200 ml of a 0.02 v/v% formalin solution of 0.005 w/v% citric acid.

Operation

Reagents (1), (2) and (3) were, respectively, placed in a cabinet-size pan. The sample was first immersed in the pan of reagent (1) for 25 minutes and removed from the pan, followed by immersing in the reagent (2) thereby causing the silver staining solution to penetrate into the gel. The sample was immersed in a pan containing 200 ml of distilled water and washed. This procedure was repeated three times. Finally, the washed sample was immersed in reagent (3) for 15 minutes to form a brown to black band image.

EXAMPLE 4

Sample

Same as used in Example 3

Reagents (1) Washing and fixing solution
Methanol, ethanol and polyethylene glycol 2000 were diluted with distilled water to make a total volume of 200 ml with concentrations of 40% (v/v), 10% (v,v) and 2% (w/v), respectively.

(2) Silver staining solution
Silver nitrate, ammonia and sodium hydroxide were dissolved in distilled water to have mixing ratios by molecular weight of 1:7:4.3. The total volume was brought up to 200 ml.

(3) Developer
Same as used in Example 3.

Operation

The operation of Example 3 was repeated using the reagents indicated above, thereby obtaining a band image similar to the image of Example 3.

EXAMPLE 5

Sample

Same as used in Example 3.

Reagents (1) Washing and fixing solution

Isopropanol and polyoxyethylene phenol (commercial name of Rhom Haas Co., Ltd., of U.S.A.: Nonizet P-40) were diluted with distilled water in concentrations of 50% (v/v) and 3% (v/v) to make a total volume of 200 ml.

(2) Silver staining solution

Silver nitrate, ammonia and sodium hydroxide were dissolved in ratios by molecular weight of 1:9.1:25.5 to make a total volume of 200 ml.

(3) Developer

Same as used in Example 3.

Operation

The procedure of Example 3 was repeated using the reagents indicated above, thereby obtaining a band image similar to the image of Example 3.

EXAMPLE 6

Sample

Same as used in Example 3.

Reagents (1) Washing and fixing solution

Same as used in Example 3.

(2) Silver staining solution

Silver nitrate, tris(hydroxymethyl)aminomethane and sodium hydroxide were dissolved in distilled water in ratios by molecular weight of 1:5:1.0 to make a total volume of 200 ml.

(3) Developer

Same as used in Example 3.

Operation

The procedure of Example 3 was repeated using the reagents indicated above, thereby obtaining a band image similar to the image of Example 3.

What is claimed is:

1. A silver staining method, which comprises
    pretreating a carrier, said carrier having disposed thereon a substance to be detected, with a solution containing from about 20 to about 90 (v/v) % of an alcohol, said solution further containing a polyethylene glycol having an average molecular weight of from about 600 to about 3500 or a polyoxyethylene alkyl phenol represented by the formula

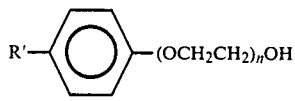

wherein R' represents a linear or branched alkyl group having from 6 to 10 carbon atoms, and n is an integer of from 7 to 10, wherein said polyethylene glycol or polyoxyethylene alkyl phenol is contained in said solution in a concentration of from about 0.05 to 5 (w/v) %, and
    treating the pretreated carrier with a solution, which comprises silver nitrate, a compound of the formula R—$NH_2$, wherein R—$NH_2$ represents ammonia or a primary amine, and a caustic alkali, in ratios by molecular weight of 1:4.5–9.5:1.0–26.0.

2. The method of claim 1, wherein the average molecular weight of the polyethylene glycol is from about 1500 to about 2500.

3. The method of claim 1, wherein R' in the polyoxyethylene phenol is octyl and n is 9.

4. The method of claim 1, wherein the concentration of the polyethylene glycol or polyoxyethylenealkyl phenol is about 2 (w/v)%.

5. The method of claim 1, wherein the alcohol is used as an aqueous solution having a concentration of from about 30 to about 70 (v/v)% of said alcohol.

6. The method of claim 1, wherein said alcohol is linear or branched and has from 1 to 4 carbon atoms, inclusive.

7. The method of claim 1, wherein said alcohol is methanol, ethanol, propanol, isopropanol, butanol, isobutanol, or mixtures thereof.

8. The method of claim 1, wherein said alcohol is isopropanol or a mixture of methanol and ethanol.

9. The method of claim 1, wherein R—$NH_2$ is ammonia, ethanolamine, propanolamine, isopropanolamine, butanolamine, isobutanolamine, tris(hydroxymethyl)aminomethane, methylamine, ethylamine, propylamine, butylamine, or isobutylamine.

10. The method of claim 1, wherein said caustic alkali is sodium hydroxide or potassium hydroxide.

11. The method of claim 1, wherein after said treating step said carrier is further immersed in a solution of from about 0.5 to about 2 (w/v)% chloroauric acid.

12. The method of claim 1, wherein said carrier is a polymerized gel.

13. The method of claim 12, wherein said polymerized gel is polyacrylamide gel, agar-agar, or agarose.

* * * * *